United States Patent [19]

Baba

[11] 3,957,441

[45] May 18, 1976

[54] COMBUSTION TUBE

[76] Inventor: Shigeo Baba, No. 7649, Fuchuh, Tokyo, Japan

[22] Filed: Dec. 10, 1973

[21] Appl. No.: 423,100

[30] Foreign Application Priority Data
Dec. 11, 1972 Japan............................ 47-124138

[52] U.S. Cl. .............................. 23/259; 23/230 M; 23/230 PC; 23/253 PC; 431/326
[51] Int. Cl.² ..................... G01N 31/12; F23D 3/40
[58] Field of Search ........... 23/259, 253 PC, 230 M, 23/230 PC; 431/326

[56] References Cited
UNITED STATES PATENTS

| | | | |
|---|---|---|---|
| 2,880,071 | 3/1959 | Gelman......................... | 23/254 E X |
| 3,205,045 | 9/1965 | Von Lossberg................. | 23/253 PC |
| 3,235,336 | 2/1966 | Matsuyama..................... | 23/253 PC |
| 3,529,937 | 9/1970 | Ihara et al...................... | 23/253 PC |
| 3,544,277 | 12/1970 | Lysyj et al. .................... | 23/253 PC |
| 3,677,714 | 7/1972 | Ledgett............................. | 23/285 |
| 3,826,614 | 7/1974 | Capuano......................... | 23/253 PC |

*Primary Examiner*—Morris O. Wolk
*Assistant Examiner*—Barry I. Hollander
*Attorney, Agent, or Firm*—Toren, McGeady and Stanger

[57] ABSTRACT

A combustion tube for preparing samples for analysis of pollution materials, such as mercury and lead, or isotopes such as tritium and carbon 14, having at least one group of oxygen-supplying tubes disposed downstream in the tube relative to an organic sample and the direction of the oxygen flow. The combustion tube is surrounded by coiled heating wire to heat the interior of the tube to cause combustion of the sample. A gas inlet is provided upstream of the sample for the injection of oxygen, nitrogen, or the like, and a gas outlet is provided at the extreme downstream end of the tube for the exhaustion of gases contained in the tube. Complete combustion of the sample is assured by providing capillary apertures in the oxygen-supplying tubes for the oxygen to exit therefrom in a fine stream.

2 Claims, 2 Drawing Figures

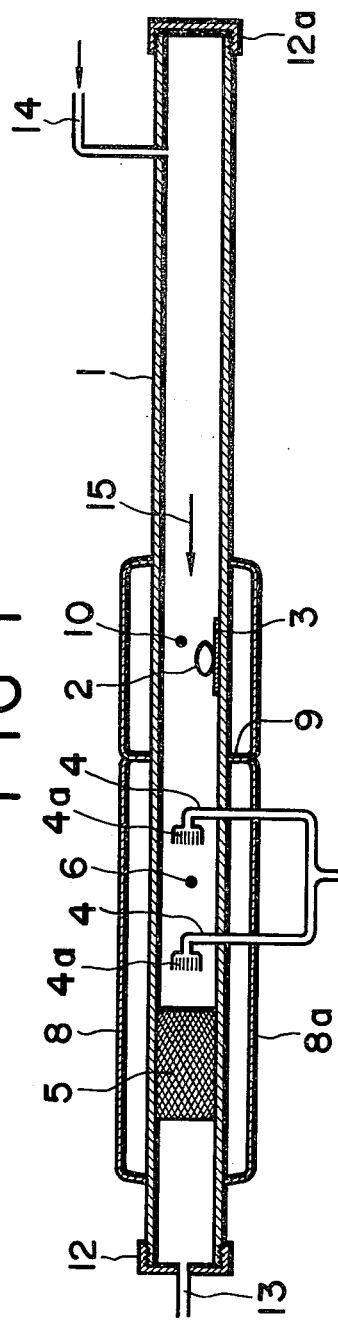
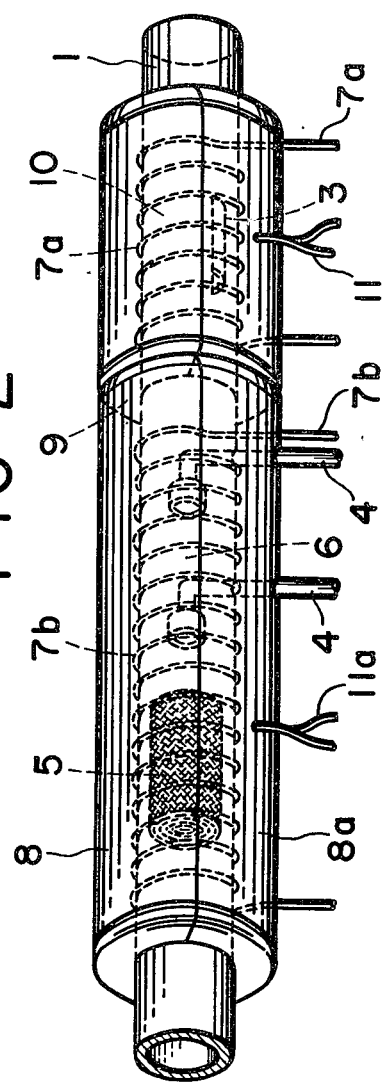

3,957,441

COMBUSTION TUBE

SUMMARY OF THE INVENTION

This invention relates to a combustion tube for preparing samples for analysis of pollution materials and isotopes in organic samples.

Substances such as mercury and lead contained in organic bodies are quite important as the trigger of toxic symptoms caused by pollution and therefore simple and quick assay methods apparatus have been required.

Heretofore, in order to prepare samples for analysis of mercury, lead or the like substance, there has been provided a decomposition of an organic sample by heating it with a mixture of sulfuric acid and nitric acid, and a decomposition of a dry sample by heating it in a flow of air or oxygen, or a like preparation method. These prior preparation methods have disadvantages such as difficulty of treating a large number of samples within a short period of time.

Furthermore, in order to decompose organic samples containing $^3H$ and $^{14}C$, there have been provided methods that include (1) wet oxidation with chromic acid for $^{14}C$,; (2) combustion of the dry organic sample in a closed vessel filled with oxygen; and (3) combustion in a flask under flowing oxygen. The methods of (1) and (2) hereinabove are not suitable for the purpose of preparing a large number of samples, and method (3) is dangerous though convenient for a rapid preparation of samples, and has caused imperfect combustion. Also, in accordance with method (3), the large combustion vessel requires an unnecessarily long time for removing $^3H_2O$ or $^{14}CO_2$. Furthermore, there is a danger of explosion due to the back flow of fluorescence in the $^{14}CO_2$ absorption tube by a small drop in temperature of the flask. Furthermore, it requires a big attachment and as a result these types of combustion apparatus are expensive.

The present invention has been completed to improve the disadvantages of the prior art hereinabove described.

Accordingly, it is an object of the present invention to provide a combustion tube for preparing samples for analysis of pollution materials in organic samples wherein in order to change the easily vaporized metal such as mercury and not easily vaporized metal such as lead in organic samples to non-vaporized inorganic salt, the combustion of the organic sample is completed within a short time.

It is another object of the present invention to provide an improved combustion tube wherein the organic sample is easily combusted within an extremely short period of time in order to change the $^3H$ and $^{14}C$ in the organic sample to $^3H_2O$ and $^{14}CO_2$ by oxidixing the organic sample in an oxygen flow.

To achieve the object of the present invention hereinabove described, one or more groups of oxygen supplying tubes are disposed in a combustion tube to accomplish complete combustion within an extemely short time by ejecting the oxygen from a large number of capillary holes of the supplying tubes.

BRIEF DESCRIPTION OF THE DRAWING

The figures in the drawing illustrate the combustion tube of the present invention for preparing samples for analysis of pollution materials, tritium and carbon 14 therein.

FIG. 1 is a schematic illustration and
FIG. 2 is an enlarged diagrammatical illustration of the essential part of the present invention.

DETAILED DESCRIPTION OF THE INVENTION

Referring to the attached drawings, the embodiment of the present invention will be explained.

In the drawings, numeral 1 is a combustion tube, said combustion tube 1 comprising a quartz glass tube or high quality glass tube of inner diameter 20 mm and length of about 400 mm in this embodiment. In the combustion tube 1, the setting position 3 for organic sample 2 is set in and one or more groups of oxygen supplying tubes 4 are disposed downstream of the organic sample setting position in the direction of the oxygen flow (left side of sample setting position 3 in the drawings). At the top of the oxygen supplying tubes 4, a large number of capillary holes 4a are disposed and oxygen is ejected therefrom. Numeral 5 is a high heating part and this high heating part is made of a platinum net. High heating part 5, comprising spiraly coiled platinum net, is arranged downstream from the oxygen supplying tubes 4 to prevent imperfect combustion of sample 2 (left side of oxygen supplying tubes 4 in the drawing). In this embodiment, combustion space 6 and high heating part 5 are heated to about 800°C. in operation, and the area around the sample setting position 3 for sample 2 can be heated up to about 600°C. within a few seconds. Combustion tube 1 is electrically heated directly through nichrome wire 7a, 7b roughly coiled on the outside of the tube 1 for observing the condition of inner part of combustion tube 1. The heating part of the combustion tube 1 is covered, in order to prevent heat release, by a quartz or glass heat release prevention cover 8, 8a. Numeral 9 is a barrier plate mounted in the heat release prevention cover, and has the function of dividing the heat gradient between heating space 10 in which the sample in combustion tube 1 is set and combustion space 6 in which the oxygen supplying tubes 4 are connected. In the drawings, numerals 11, 11a is thermocouple thermometers, numerals 12, 12a are detachable cover caps on the both ends of the combustion tube 1, numeral 13 are a gas outlet through cover cap 12 and numeral 14 is an oxygen or nitrogen gas inlet connected to the combustion tube.

An organic sample 2 put in the sample setting position 3 in the combustion tube 1 hereinabove constructed is electrically heated by nichrome wire 7a to decompose as combustible gas at the setting position 3. The combustion gas is forced in the direction of arrow 15 in FIG. 1 by a small amount of oxygen flow supplied from inlet 14 connected in combustion tube 1. The admitted gas at combustion space 6 where the oxygen supplying tube 4 is ignited in a large amount of oxygen gas ejected from oxygen supplying tubes 4 are disposed. In prior known combustion tubes. oxygen is supplied by a single gas inlet 14, therefore long hours are required to complete the combustion due to oxygen deficiency. On the contrary in the combustion tube of the present invention, the organic sample can be ignited immediately by supplying a large amount of oxygen from the oxygen supplying tubes 4.

Further when supplying the oxygen from a single inlet, imperfect combustion occurs at sample setting position 3, and imperfect combustibles (soot) is admitted to a gas trap (not shown in the drawings) through the gas outlet 13, thereby making quantitative recovery impossible. However, as hereinabove explained, soot formed by imperfect combustion and attached on the inner wall of the combustion tube is ignited within a few seconds by supplying additional oxygen. Insertion of the sample into the sample setting position 3 causes the sample to scatter by the sudden vaporization of water. Therefore, the sample heating part 10 should be cooled when combustion is finished.

The combustion tube of the present invention has the following advantages:

1. The required time for perfect combustion of the organic sample is reduced by setting one or more groups of oxygen supplying tubes downstream of the organic sample setting position as compared with a combustion tube having a single oxygen inlet 14.
2. $^3H_2O$ or $^{14}CO_2$ gas is effectively expelled using the combustion tube of this type instead of the prior oxygen flask. Sample preparation apparatuses for $^3H$ and $^{14}C$ analyzers can be made at a low price due to the lack of complicated attachment.
3. Direct electric heating by nichrome wires instead of using an electric furnace makes possible the direct observation of the combustion condition, and easy control of the temperature of the tube. The heat capacity of nichrome wire is smaller than that of an electric furnace, thereby making possible the insertion of another sample immediately after finishing the combustion.

The manner of operation of the combustion tube of the present invention will be explained with the preferred embodiment.

EMBODIMENT OF OPERATION 1

Combustion space 6 and high heating part 5 comprising platinum net are heated constantly at 600° – 800°C by nichrome wire 7b. An organic sample 2 on a platinum boat is inserted into the sample setting position 3 and tightly stoppered with cover cap 12a.

Oxygen is admitted through the gas inlet 14 at 100 ml/min. and through the oxygen supplying tubes 4 at about 500 ml/min. immediately after supplying electric current through nichrome wire 7a, and heating space 10, where sample 2 is set in sample setting position 3, is heated. Combustion is mainly continued at combustion space 6 and completed within a short time. Wet biological samples weighing 500 mg. can be ignited within 3 minutes.

Vaporized mercury is trapped in a vessel containing potassium permanganate solution (not shown in the drawings) and passes through gas outlet 13 leaving lead as an inorganic salt in the platinum boat.

After the completion of combustion, electric current through nichrome wire 7a is cut off followed by stopping the oxygen supply, and mercury vapor in the combustion tube is completely exhausted by admitting nitrogen gas through the gas inlet 14 for about 15 seconds.

Trapped mercury and remaining lead can be analysed in the usual manner.

EMBODIMENT OF OPERATION 2

Biological sample containing $^3H$ and/or $^{14}C$ are ignited according to the embodiment of operation 1. $^3H_2O$ formed is trapped in a cooling trap and $^{14}CO_2$ is absorbed in a fluorescence containing basic substance. Nitrogen gas is admitted through inlet 14, after combustion is completed, expelling oxygen dissolved in water containing $^3H_2O$ and fluorescence to inhibit the $^{14}C$ and $^3H$ assay. Trapped $^3H_2O$ and $^{14}CO_2$ can be analysed in the usual manner.

What I claim is:

1. A combustion tube for preparing a sample from an organic body comprising an axially elongated tube; an oxygen supply tube located at one axial end of said elongated tube; a gas outlet opening located at the other axial end of said elongated tube downstream of said oxygen supply tube; a sample heating space within said elongated tube downstream of said oxygen supply tube; a combustion station downstream of said sample heating space and including at least one oxygen supply tube having a plurality of capillary apertures formed therein for the oxygen to flow therethrough said plurality of capillary apertures being symmetrically disposed about and close to the longitudinal axis of said elongated tube; a high-heating part downstream of said at least one oxygen supply tube comprising a platinum net; heating means surrounding said sample heating space said combustion station and said high-heating part, said heating means comprising a first heating wire wound about one part of said elongated tube, and a second heating wire wound about another part of said elongated tube; a covering surrounding said heating means mounted on said elongated tube for preventing heat release therefrom; and a barrier plate mounted inside said covering for thermally insulating said first wire from said second wire, said barrier plate thermally dividing said one and said another part of said elongated tube.

2. The combustion tube according to claim 1, wherein said combustion station comprises a plurality of said oxygen supply tubes located at said combustion station, said plurality of oxygen supply tubes located at said combustion station being parallelly spaced along the axial direction of said elongated tube, and each of said plurality of oxygen supply tubes having a plurality of said capillary apertures formed therein.

* * * * *